US 6,488,631 B2

(12) United States Patent
Ohara et al.

(10) Patent No.: US 6,488,631 B2
(45) Date of Patent: Dec. 3, 2002

(54) ULTRASONIC ENDOSCOPE

(75) Inventors: Kenichi Ohara, Gunma; Toshiyuki Hashiyama, Saitama, both of (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/987,281

(22) Filed: Nov. 14, 2001

(65) Prior Publication Data

US 2002/0062083 A1 May 23, 2002

(30) Foreign Application Priority Data

Nov. 21, 2000 (JP) ........................................ 2000-353739

(51) Int. Cl.⁷ ................................................ A61B 8/00
(52) U.S. Cl. ........................ 600/462; 600/459; 600/466
(58) Field of Search ................... 600/459, 463; 29/25.35

(56) References Cited

U.S. PATENT DOCUMENTS 5,044,053 A * 9/1991 Kopel et al. ............... 29/25.35
5,876,345 A * 3/1999 Eaton et al. ................ 600/463
6,149,598 A * 11/2000 Tanaka ....................... 600/437
6,228,032 B1 * 5/2001 Eaton et al. ................ 600/463

* cited by examiner

Primary Examiner—Marvin M. Lateef
Assistant Examiner—Ruby Jain
(74) Attorney, Agent, or Firm—Greenblum & Bernstein, P.L.C.

(57) ABSTRACT

An ultrasonic endoscope has a bending portion, an ultrasonic probe, and a flexible circuit board. The bending portion, connected to the point of a flexible tube, bends along two predetermined bending-directions perpendicular to each other, by remote control. The ultrasonic probe has a plurality of ultrasonic wave vibrators, which are arranged circumferentially, and send ultrasonic waves radially and receive echoes of the ultrasonic waves. The flexible circuit board, which transmits signals associated with the ultrasonic waves and the echoes, is constructed of a plurality of flexible circuit board strips in the bending portion so as to allow a bending motion. The plurality of flexible circuit board strips are arranged such that a bending-resistance to the bending motion occurs symmetrically with respect to a primary central line, corresponding to one of the two bending-directions.

11 Claims, 12 Drawing Sheets

ULTRASONIC ENDOSCOPE

BACKGROUND OF THE INVENTION

1. Field of the Invention

The present invention relates to an ultrasonic endoscope, which uses ultrasonic waves for the diagnosis of a diseased tissue. Especially, the present invention relates to the construction of the distal end of the ultrasonic endoscope.

2. Description of the Related Art

In the ultrasonic endoscope, an ultrasonic probe having ultrasonic wave vibrators is provided at the distal end of the endoscope. The ultrasonic probe sends ultrasonic waves and receives echoes of the sent ultrasonic waves.

For the scanning method, a radial scanning or a linear scanning is used. For example, when diagnosing an organ (body-cavity), into which the ultrasonic endoscope cannot be inserted, the radial scanning is performed. The endoscope is inserted toward an organ adjacent to the observed organ, ultrasonic waves are sent radially from the ultrasonic probe. Conventionally, a mechanical-type radial scanning is applied, where a series of ultrasonic wave vibrators is aligned along an axis of the probe and revolves on the axis to send the ultrasonic waves radially.

However, in the case of the mechanical type radial scanning, a color-image, partially colored by Red (R), G (Green), B(Blue), which is effective for diagnosis of the diseased areas, cannot be displayed on the monitor.

Further, in an ultrasonic endoscope, the solid or hard ultrasonic probe is provided at the distal end of the endoscope. Therefore, when moving the endoscope towards the observed portion, it is important not to cause pain with the attachment at the distal end portion. To facilitate this, a far greater response performance of the bending portion to the operator's manipulation is required compared to a normal endoscope.

SUMMARY OF THE INVENTION

Therefore, an object of the present invention is to provide an ultrasonic endoscope that is capable of obtaining an observed-image effective for diagnosis without degrading the response performance of the bending portion.

An ultrasonic endoscope according to the present invention is an endoscope for performing electronic radial scanning. A bending portion formed in a tube is connected to the point of a flexible tube, which is inserted in a body, or organ. The flexible tube is normally connected to a manipulator portion of the endoscope, and an operator, such as doctor, bends the bending portion by manipulating a manipulating knob, which is operatively connected to the bending portion. Namely, the bending portion bends by remote control.

The bending portion bends along two predetermined directions. Normally, the bending portion bends along an up-down direction and a left-right direction, which are perpendicular to each other. The up-down direction and the left-right direction are defined on the basis of the holding-posture of the manipulator portion, the connection between the manipulator portion and the flexible tube, and so on. The manipulating knob for bending the bending portion toward the up, down, left, or right direction, is provided at the manipulator portion, and the operator manipulates the manipulating knob as required. For example, the manipulating knob is composed of an up-down knob for bending the bending portion along the up-down direction and a left-right knob for bending the bending portion along the left-right direction.

The ultrasonic endoscope is a fiber-scope type endoscope or a video-scope type endoscope. In the case of the video-scope type endoscope, the ultrasonic endoscope is connected to a video-processor having a light source and signal circuits and is connected to an exclusive ultrasonic wave diagnosis apparatus. An image sensor is provided at the distal end of the endoscope, and further, an image signal cable connected to the image sensor, a fiber-optic bundle for the light source, a delivery tube for providing liquid or air, and a forceps tube for inserting a forceps, are arranged in the endoscope. On the other hand, in the case of the fiber-scope type endoscope, the ultrasonic endoscope is connected to a light source unit and is then connected to the ultrasonic wave diagnosis apparatus. Further, an image fiber-optic bundle for optically transmitting the object image is provided in the endoscope, in place of the image signal cable. Note that, the fiber-optic bundle for the light source and the delivery tube may be composed of a pair of fiber-optic bundles and a pair of delivery tubes, respectively.

An ultrasonic probe for the electronic radial scanning is operatively connected to the bending portion. For example, a solid point-base portion is connected to the bending portion and the ultrasonic endoscope is attached to the point-base portion.

The ultrasonic probe has a plurality of ultrasonic wave vibrators, which are arranged circumferentially to perform the electronic radial scanning. The plurality of ultrasonic wave vibrators send ultrasonic waves radially around a center axis of the ultrasonic probe and receive echoes of the ultrasonic waves.

According to the present invention, a flexible circuit board is provided in the endoscope. The flexible circuit board transmits signals associated with ultrasonic waves and echoes, so that an ultrasonic-image, representing a section-image in the body, is obtained at the ultrasonic wave diagnosis apparatus. As electronic scanning (not mechanical scanning) is performed, an ultrasonic color-image is obtained as required by simultaneously sending multiple ultrasonic waves, each frequency of which is different, or an ultrasonic pulse-width image is obtained by coloring in accordance with contrast of the echoes. These images cannot be obtained by mechanical radial scanning.

In the bending portion, the flexible circuit board is constructed of a plurality of flexible circuit board strips so as to allow a bending motion, namely, to be capable of withstanding the bending motion. The plurality of flexible circuit board strips extends along a central axis of the bending portion. Since the signal-transmitting member in the bending portion is composed of a plurality of flexible circuit board strips, snapping does not occur while the bending portion is manipulated. The plurality of flexible circuit board strips enables the circumferential arrangement of the ultrasonic wave vibrators, namely, the electronic radial scanning. Note that, the width of each flexible circuit board strips is defined in accordance with a radius of the bending portion.

Further, according to the present invention, the plurality of flexible circuit board strips are arranged in the bending portion such that an excellent response performance for the bending manipulation is realized. Note that, the response performance represents whether the bending portion bends along the determined direction precisely without inclining in an undetermined direction. While inserting the flexible tube into the organ, the operator, as required, bends the bending portion along only one of two directions, or one of the up-down direction and the left-right direction, to pass the flexible tube through the organ smoothly. Almost all operators bend the bending portion along the up-down direction. Speaking concretely, most operators insert the flexible tube by bending the bending portion toward the up-direction and returning it toward the neutral position, as required.

In the endoscope of the present invention, the plurality of flexible circuit board strips are arranged in the bending portion such that a bending-resistance to the bending motion occurs symmetrically with respect to a primary central line. The primary central line is defined on a section of the bending portion, crosses the central axis of the bending portion, and corresponds to one of the two bending-directions (normally, the up-down direction). The plurality of flexible circuit board strips are arranged in accordance with the arrangement of the various members extending through the bending portion, such as the fiber-optic bundle, the delivery tube, and the forceps tube.

As the bending-resistance (flexural-resistance) occurs symmetrically, in other words, the flexural rigidity along the direction to be bent has symmetry with respect to the primary central line, the response performance to the bending manipulation is excellent and the bending portion bends toward the desired direction precisely. Therefore, when inserting the flexible tube, the operator can manipulate the bending portion so as not to cause a pain to the patient.

To produce a bending-resistance having precise symmetry, preferably, each members provided in the endoscope, such as the fiber-optic bundle, the delivery tubes, and so on, is arranged so as to have symmetry with respect to the primary central line on the section. For example, in the case of the video-scope type endoscope, the fiber-optic bundle, the delivery tube, the forceps tube, and the image signal cable are arranged so as to have symmetry with respect to the primary central line. Then, the plurality of flexible circuit board strips are arranged so as to have symmetry with respect to the primary central line in the section. Therefore, a bending portion with high response performance to the bending motion is easily arranged, or manufactured.

To arrange the plurality of circuit board strips without difficulty, preferably, the width and thickness of each of the plurality of circuit board strips on the section is substantially the same.

To securely and easily arrange the plurality of circuit board strips symmetrically, and to maintain the symmetrical arrangement during the bending motion, a plurality of bundles, each of which is composed of at least two flexible circuit board strips, may be formed. For example, if the number of circuit board strips is even, each bundle can be composed of two flexible circuit board strips. The plurality of flexible circuit board strips bends in each bundle, namely, the flexure direction is the same in each bundle. Therefore, the bending-resistance to the bending motion is stable and occurs symmetrically.

When the section form of the circuit board strips flexes, the bending-resistance to the bending motion tends to occur unsymmetrically. To produce a bending-resistance having precise symmetry, preferably, the plurality of circuit board strips are arranged along the central axis such that the section-form of each of the plurality of circuit board strips becomes substantially straight. In this case, each flexible circuit board strip bends smoothly, and the bending-resistance is stable and occurs symmetrically.

To maintain the symmetrical arrangement during the bending motion of the bending portion, the plurality of circuit board strips may not be positioned on a line of action, namely, the primary central line. Namely, preferably, the plurality of circuit board strips are arranged such that the plurality of circuit board strips are not on the primary central line in the section.

As for the total construction of the flexible circuit board, the flexible circuit board may be composed of the flexible circuit board strips (pieces), which are connected to the ultrasonic wave vibrator separately. However, in order to easily arrange the flexible circuit board so that it is symmetrical in the bending portion, preferably, the flexible circuit board is formed by partially cutting a single rectangular flexible circuit board such that a plurality of flexible circuit board strips are formed. Then, the cut rectangular flexible circuit board is rounded so as to form a cylinder. The strip portions are then gathered together at the end furthest from the board and a cone-like structure is formed. The plurality of circuit board strips may be arranged such that they are not on the primary central line in the section.

To symmetrically and easily arrange, preferably, the number of flexible circuit board strips is eight, and the width of each strip is substantially the same. Further, preferably, the eight circuit board strips are bundled such that two adjacent circuit board strips form one bundle.

BRIEF DESCRIPTION OF THE DRAWINGS

The present invention will be better understood from the description of the preferred embodiment of the invention set fourth below together with the accompanying drawings, in which.

DESCRIPTION OF THE PREFERRED EMBODIMENTS

Hereinafter, the preferred embodiments of the present invention are described with reference to the attached drawings.

Figure 1:
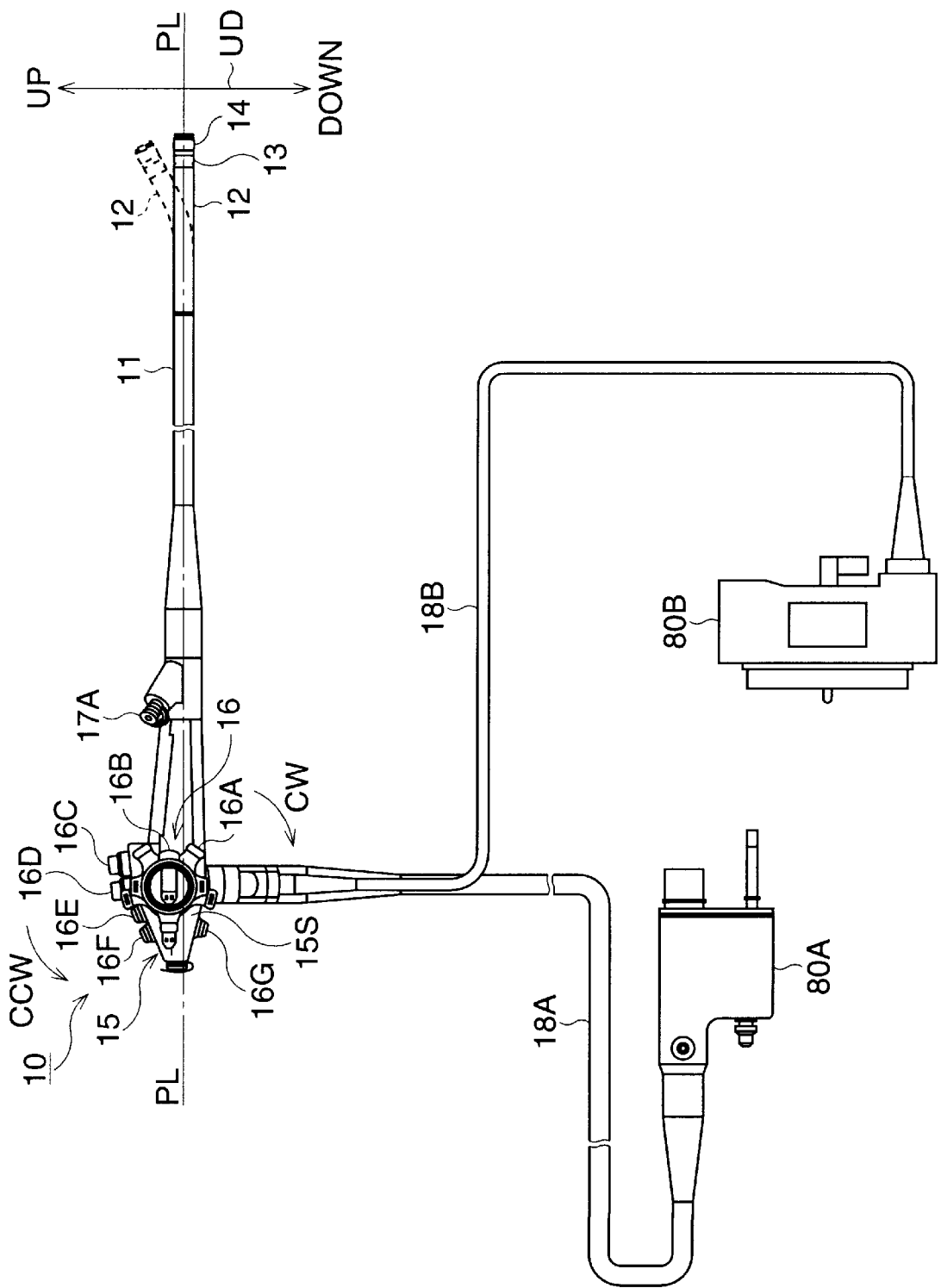
FIG. 1 is a side view of an ultrasonic endoscope of a first embodiment.
Figure 2:
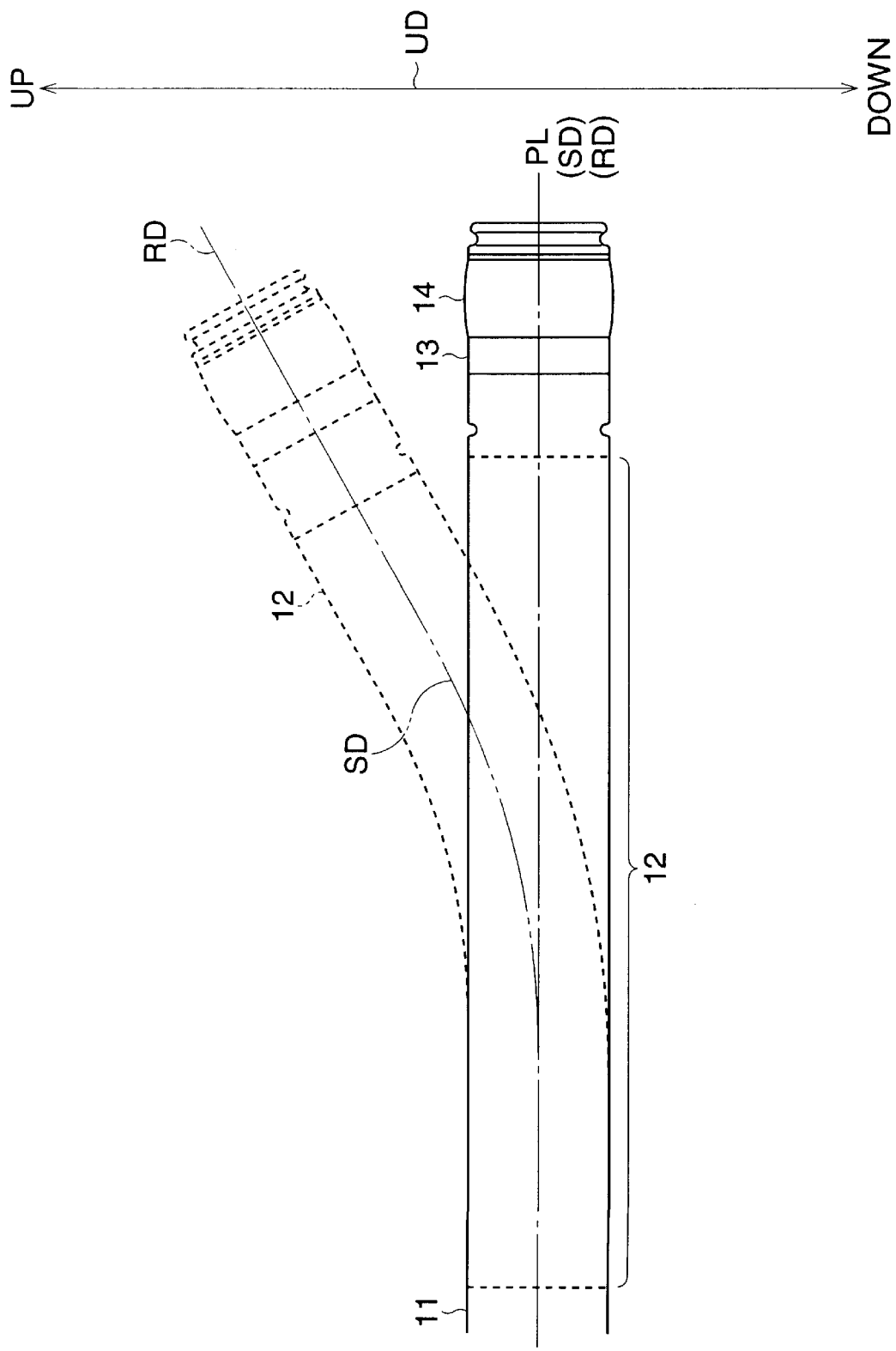
FIG. 2 is a view showing a portion of the point of the ultrasonic endoscope.

FIG. 1 is a side view of an ultrasonic endoscope of the first embodiment. FIG. 2 is a view showing a portion of the point of the ultrasonic endoscope.

An ultrasonic endoscope 10 has a flexible tube 11, manipulator portion 15, first and second connected tubes 18A and 18B, and first and second connecters 80A and 80B. A bending portion 12, a point-base portion 13 and an ultrasonic probe 14 are provided at the distal end of the flexible tube 11, namely, the distal end of the endoscope 10.

The bending portion 12 is connected to the point of the flexible tube 11, the point-base portion 13 is attached to the bending portion 12, and the ultrasonic probe 14 is attached to the point-base portion 13. The first and second connecters 80A and 80B are connected to the first and second connected tubes 18A and 18B respectively, and the first and second connected tubes 18A and 18B are connected to the manipulator portion 15. The flexible tube 11, which is inserted into a given organ (body-cavity), is connected to the manipulator portion 15.

When performing the diagnosis, the first connecter 80A is connected to a video-processor (not shown) having a light source and signal processor circuits, the second connecter 80B is connected to an ultrasonic wave diagnosis apparatus (not shown), and then the flexible tube 11 is inserted into the body-cavity. A first monitor for displaying the observed color image (not shown) is connected to the video-processor and a second monitor for displaying an ultrasonic-image (not shown) is connected to the ultrasonic wave diagnosis apparatus. An operator, such as a doctor, operates a set of manipulating knobs 16, which are composed of an up-down knob 16A and a left-right knob 16B and are provided on the manipulator portion 15, with his right hand. Then, the operator holds the flexible tube 11 in his left hand and inserts the flexible tube 11 toward observed-organ in a patient's body.

A pair of fiber-optic bundles (herein not shown) are provided between the first connector 80A and the ultrasonic probe 14, light radiated from the light source in the video-processor passes through the fiber-optic bundles and is emitted from the distal end of the fiber-optic bundles, namely, the distal end of the ultrasonic endoscope 10. Consequently, an observed-object is illuminated by the light emitted from the fiber-optic bundles.

The ultrasonic endoscope 10 functions as a video-scope. Namely, an objective lens (herein not shown) and an image sensor (not shown), such as a CCD (Charge-Coupled Device), are provided in the ultrasonic probe 14, and an image signal cable (herein not shown) connecting the image sensor and the video-processor is provided in the ultrasonic endoscope 10. The light reflected on the object portion passes through the objective lens and reaches the image sensor. Thus, the object image is formed on the image sensor and image signals corresponding to the object image are generated. The image signals are read from the image sensor and fed to the video-processor. In the video-processor, various processes are performed on the image signals, so that video signals, such as an NTSC signal, are generated. The video signals are output to the first monitor so that the object image is displayed on the first monitor.

The bending portion 12 is bent by the operator's remote control, namely, by manipulating the up-down knob 16A and/or the left-right knob 16B. The up-down knob 16A and the left-right knob 16B, provided on the right side surface 15S of the manipulator portion 15, are both rotatable dial type knobs and are connected to the bending portion via wires (herein not shown). The bending portion 12 bends along the two bending directions, namely, the up-down direction shown by "UD" and the left-right direction, by turning the up-down knob 16A and the left-right knob 16B.

In this embodiment, the bending directions are defined as follows.

When extending the flexible tube 11 so that it is straight and untwisted, a straight-line center axis PL of the flexible tube 11 is defined. In this case, a central axis of the flexible tube 11 coincides with the straight-line center axis PL. The manipulator portion 15 is formed along the straight-line center axis PL. While the bending portion 12 is in a neutral posture, the bending portion 12 extends along the straight-line center axis PL. Therefore, when defining the central axis "SD" of bending portion 12 and the central axis of the point "RD" of the solid point-base portion 13 and the solid ultrasonic probe 14, the central axis SD and the central axis of the point RD coincide with the straight-line center axis PL, as shown in FIG.2.

The bending portion 12 bends along the two bending directions, which are on a plane perpendicular to the straight-line center axis PL. The two directions, or the up-down direction UD and the left-right direction are perpendicular to each other. The up-down direction UD is generally parallel to a rotation plane, on which the up-down knob 16A revolves. When the operator holds the manipulator portion 15, the rotation plane is usually parallel to the vertical direction. The left-right direction is perpendicular to the up-down direction UD, namely, parallel to a line perpendicular to the paper's surface.

When the operator turns the up-down knob 16A counterclockwise (shown by "CCW"), the bending portion 12 bends toward the up direction, as shown by the broken line in FIG. 2. Consequently, the ultrasonic probe 14 faces a direction different from the straight-line center axis PL. Namely, the ultrasonic probe 14 has a given angle to the center axis PL. When the operator turns the up-down knob 16A clockwise (shown by "CW"), the bending portion 12 bends toward the down direction. Similarly, the bending portion 12 bends to the left and right direction by turning the left-right knob 16B counterclockwise or clockwise respectively.

When inserting the flexible tube 11, the operator manipulates the distal end of the endoscope 10 and the flexible tube 11 while watching the color image displayed on the first monitor. Speaking correctly, the operator "shakes" the manipulator portion 15 while holding the manipulating knobs 16 such that the flexible tube 11 turns, or revolves around, the central axis of the flexible tube 11. Further, the operator manipulates the up-down knob 16A clockwise CW and counterclockwise CWW with his right hand's fingers to bend the bending portion 12 in the up-down direction UD. By shaking the manipulator portion 15 and bending the bending portion 12 in the up-down direction UD, the ultrasonic probe 14, namely, the distal end of the ultrasonic endoscope 10 reaches the object portion in the organ, smoothly.

When the ultrasonic probe 14 reaches objective portion, ultrasonic wave pulse signals are output from the ultrasonic wave diagnosis apparatus and are fed to the ultrasonic probe 14 via the second connecter 80B. The ultrasonic probe 14 sends ultrasonic waves on the basis of the ultrasonic wave pulse signals and then receives the echoes of the ultrasonic waves. The echoes are transferred to pulse signals and then the pulse signals are fed to the ultrasonic wave diagnosis apparatus via the second connecter 80B. In the ultrasonic wave diagnosis apparatus, various processes are performed on the input pulse signals corresponding to the echoes, so that anultrasonic-image, which is a section image along the sending direction of the ultrasonic waves, is displayed on the second monitor.

A forceps tube (herein not shown) is provided between the manipulator portion 15 and the ultrasonic probe 14. A given forceps for treating the diseased portion is inserted from a forceps entrance 17A. Further, a pair of delivery tubes (herein not shown) for supplying water to the point-base portion 13 is provided in the ultrasonic endoscope 10. At the manipulator portion 15, a delivery switch button 16C is provided. When the delivery switch button 16C is operated, the water flows in the delivery tubes and is emitted from the side surface of the point-base portion 13. An absorption switch button 16D, a freeze switch button 16E, a copy switch button 16F, and a recording switch button 16G are provided on the manipulator portion 15. These switches 16C, 16D, 16E, 16F, and 16G are arranged along the up-down direction UD.

Figure 3:
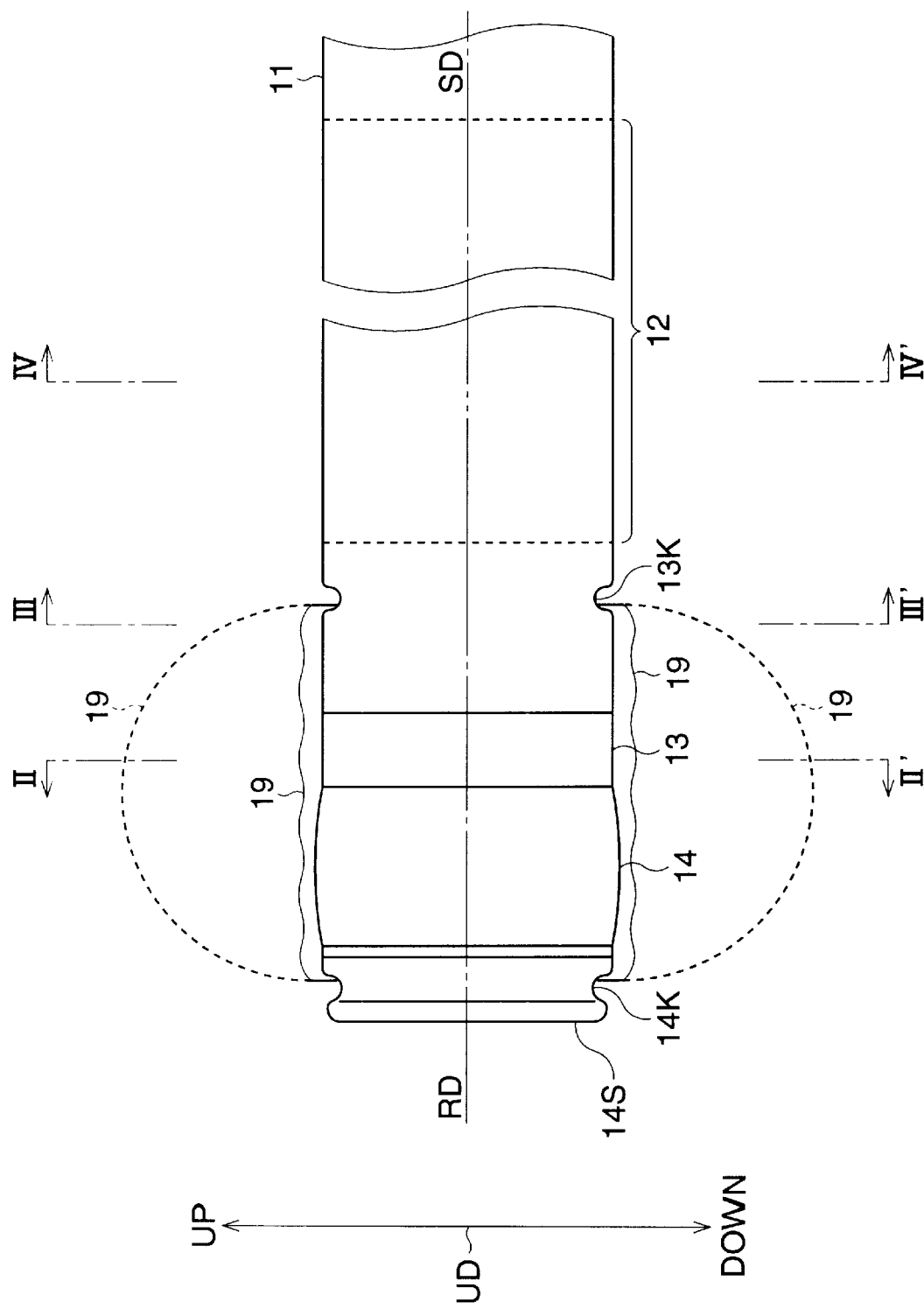
FIG. 3 is a side view showing the point-base portion and the ultrasonic probe, seen from the left side.
Figure 4:
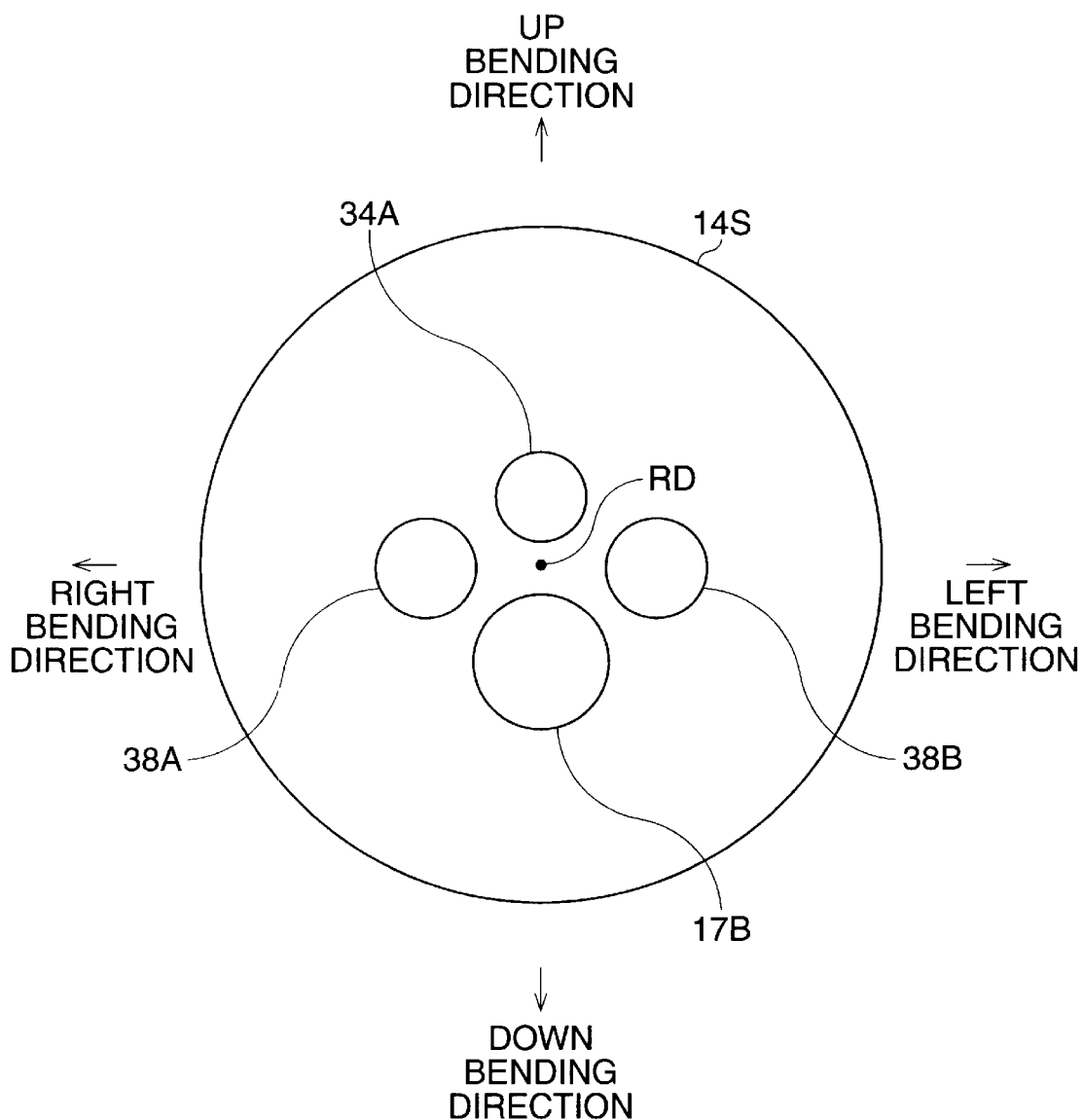
FIG. 4 is a front view of the ultrasonic probe.

FIG. 3 is a side view showing the point-base portion 13 and the ultrasonic probe 14, seen from the left side. FIG. 4 is a front view of the ultrasonic probe 14.

The stiff point-base portion 13 and the ultrasonic probe 14 are covered with a balloon 19 when performing the ultrasonic wave diagnosis. To fix the balloon 19, a first groove 14K is formed around the outer surface of the ultrasonic probe 14 and a second groove 13K is formed around the outer surface of the point-base portion 13. The water, flowing through the delivery tubes, comes out of two outlets (not shown) on the outer surface of the point-base portion 13. To obtain a precise ultrasonic image, the water in a tank (not shown) provided at the video-processor is supplied inside the balloon 19 via the couple of delivery tubes, so that the balloon 19 expands, as shown by the broken line. After the diagnosis, the water in the balloon 19 is absorbed by pushing the absorption switch button 16E and is then fed to an absorbing unit (not shown) via the couple of delivery tubes.

As shown in FIG. 4, on the front surface 14S of the ultrasonic probe 14, an objective lens 34A is provided, and emitting surfaces 38A and 38B of the fiber-optic bundles and a forceps outlet 17B of the forceps tube are formed. The light, reflected on the subject, passes through the objective lens 34A and reaches the image sensor within the ultrasonic probe 14. The objective lens 34 is provided on the front surface 14S, namely, the point surface of the ultrasonic probe 14 (not side surface) Therefore, the visual field broads along the central axis RD of the point. As the visual field substantially coincides with the direction of progress of the distal end of the endoscope 10, the operator can insert the flexible tube 11 and manipulate the manipulator portion 15 while looking at the progress of the probe 14.

Figure 5:
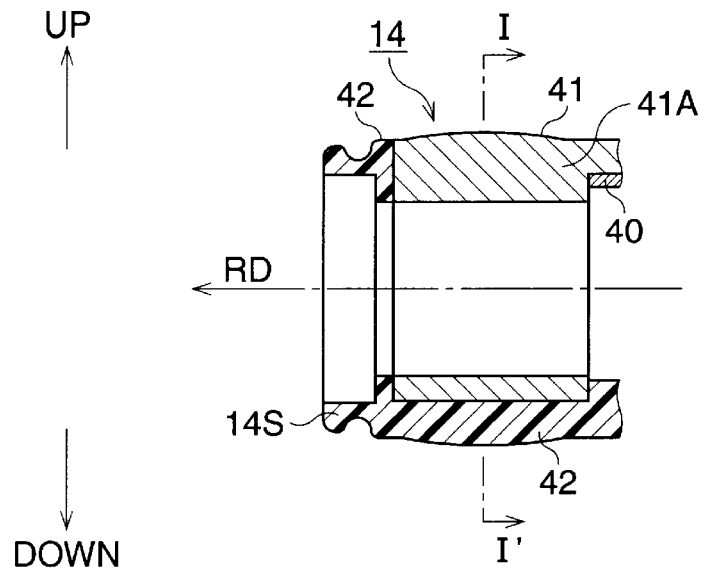
FIG. 5 is a schematic section view of the ultrasonic probe from the side, passing through the center axis of the point and along the up-down direction.
Figure 6:
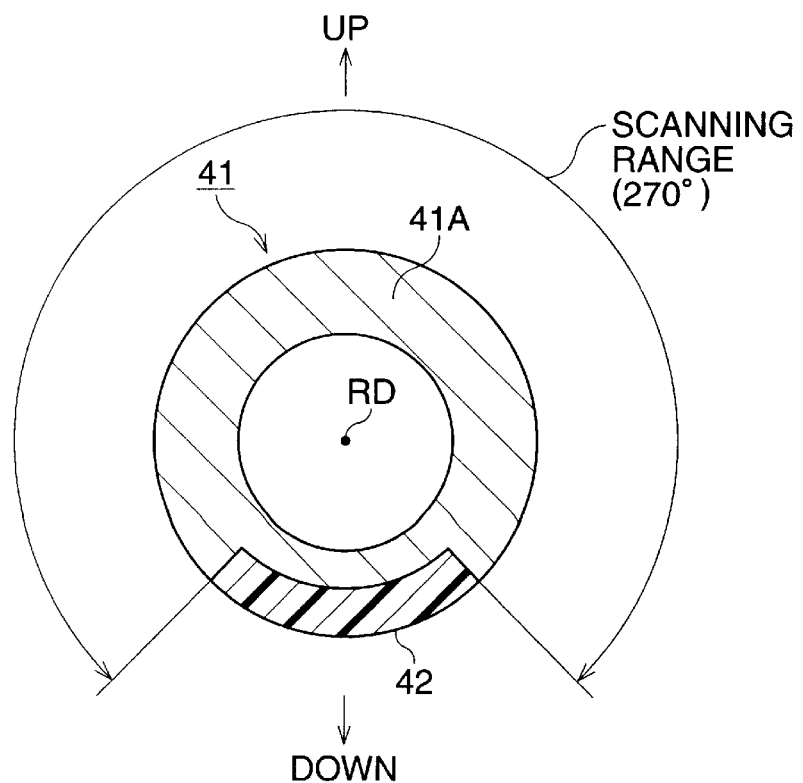
FIG. 6 is a schematic section view of the ultrasonic probe at line I–I' shown in FIG. 5, seen from the front.

FIG. 5 is a schematic section view of the ultrasonic probe 14, passing through the central axis of the point RD and along the up-down direction UD. FIG. 6 is a schematic section view of the ultrasonic probe 14 across the line I–I' shown in FIG. 5, seen from the front surface 14S. Note that, the fiber-optic bundles, forceps tubes, and the image signal cable connected to the image sensor are not shown in FIGS. 5 and 6.

The ultrasonic probe 14 includes an ultrasonic wave sender-receiver 41 and a supporting member 42. The ultrasonic wave sender-receiver 41 is formed along the circumference of the cylindrical ultrasonic probe 14, and the supporting member 42 supports the ultrasonic wave sender-receiver 41. A flexible circuit board 40 for transmitting signals associated with the ultrasonic waves and their echoes is connected to the ultrasonic wave sender-receiver 41. The ultrasonic wave sender-receiver 41 is composed of a plurality of ultrasonic wave vibrators 41A, which are arranged along the circumference of the ultrasonic probe 14 to perform the radial scanning. In this embodiment, each of the plurality of ultrasonic wave vibrators 41A is a piezoelectric element, which transfers electric signals to mechanical vibration and vice versa.

High frequency pulse signals, input to the ultrasonic wave sender-receiver 41 via the flexible circuit board 40, are transformed to ultrasonic waves by the piezoelectric effect. The ultrasonic wave sender-receiver 41 radially sends the ultrasonic waves around the central axis of the point RD, in order. Each of the ultrasonic waves is sent in accordance with a predetermined frequency and timing to perform the electronic radial scanning. In this embodiment, the scanning range is 270 degrees. When the ultrasonic wave sender-receiver 41 receives the echoes in order, the echoes are transformed to given electric signals by the inverse piezoelectric effect. The electric signals are fed to the ultrasonic wave diagnosis apparatus via the flexible circuit board 40.

Figure 7:
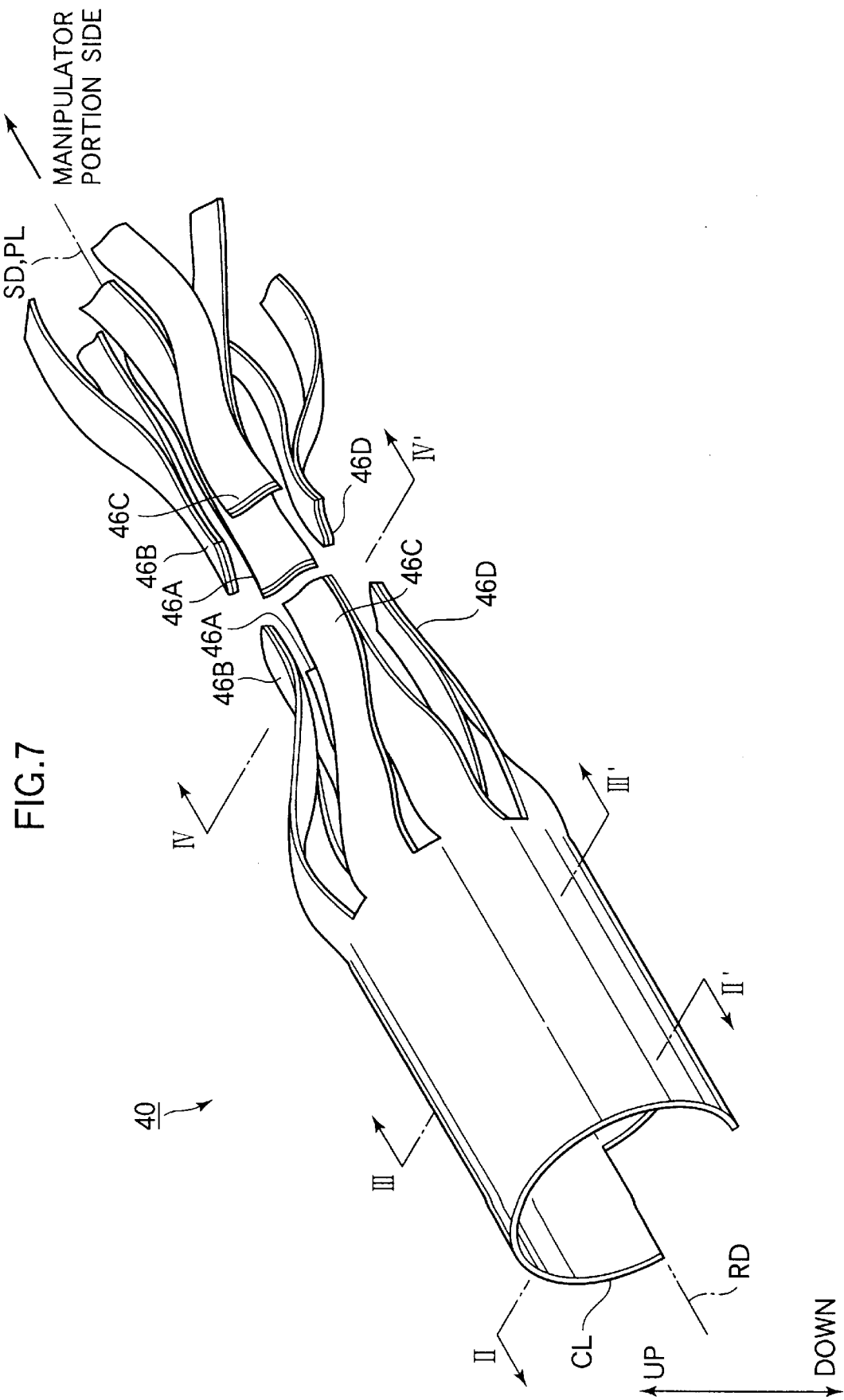
FIG. 7 is a schematic perspective view of the flexible circuit board formed in the endoscope.
Figure 8:
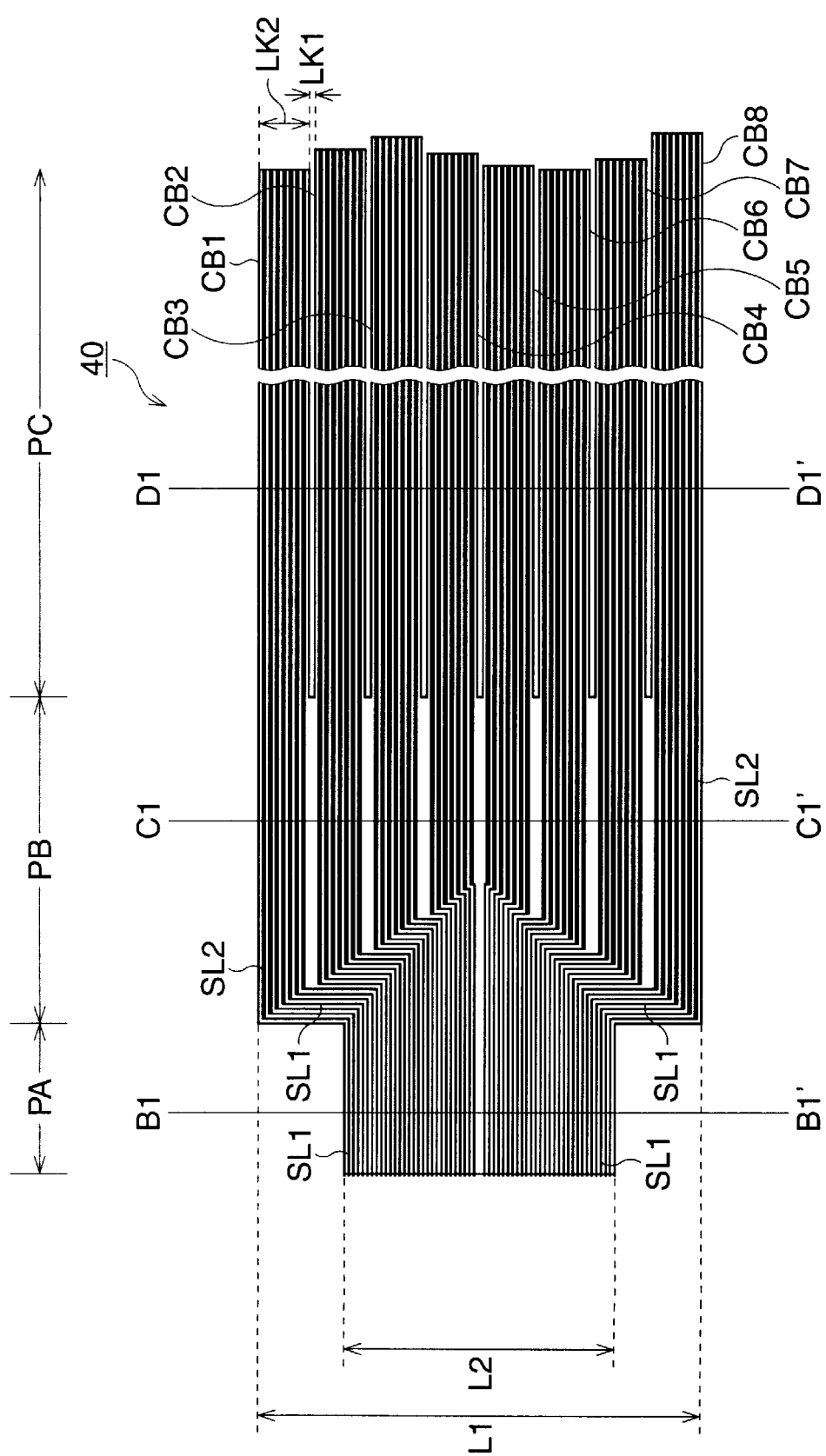
FIG. 8 is a view showing the unfolded flexible circuit board.

FIG. 7 is a schematic perspective view of the flexible circuit board formed in the endoscope 10. FIG. 8 is a view showing the unfolded flexible circuit board.

The flexible circuit board 40 is a flexible and thin substrate, on which circuits are formed. The form of the flexible circuit board 40 can be arbitrarily set, namely, the flexible circuit board 40 can be formed to make any predetermined shape as required. In this embodiment, the flexible circuit board 40 is shaped like a "cone", as shown in FIG. 7. The circumferential line portion, "CL" is connected to the arc-shaped ultrasonic wave sender-receiver 41 shown in FIG. 6. In the point-base portion 13, the flexible circuit board 40 is formed in a barrel. In the bending portion 12, the flexible circuit board 40 is constructed of a plurality of flexible circuit board strips. The plurality of flexible circuit board strips are connected to signal lines (herein not shown) extended from the second connector 80B and through the manipulator portion 15. The circuit board strips extend along the central axis SD in the bending portion 12. Note that, in FIGS. 7 and 8, part of the plurality of circuit board strips is omitted, or not shown.

The cone-shaped flexible circuit board 40 is formed by rounding the flat and rectangular flexible circuit board 40' shown in FIG. 8. In FIG. 8, sections PA and PB correspond to the range of the point-base portion 13 and the ultrasonic probe 14. Section PC corresponds to the range of the bending portion 12. The width "L2" at the section PA, namely, the length of the circumference line portion CL, corresponds to the scanning range. The width "L1" at the sections PB and PC, greater than the width "L2", corresponds to a circumferential length of the point-base portion 13 and the bending portion 12. At the section PC, namely, corresponding to the range of the bending portion 12, the rectangular flexible circuit board 40', is divided into the eight strips. Each interval "LK1" between a circuit board strip and adjacent circuit board strip is equal and the width "LK2" of each circuit board strip is equal. Note that, the longitudinal length is different in each circuit board strips. Hereinafter, the eight circuit board strips are designated by "CB1, CB2, . . . , and CB8".

On the rectangular flexible circuit board 40', printed wirings, namely, conduct lines are formed. Printed wiring SL2, formed in the section PB and the section PC, is bolder than the printed wiring SL1 formed in the section PA. Note that, printed wiring is not shown in FIG. 7. The boldness of each signal line of the printed wiring SL2 depends upon the width "L1" and the width "LK2". The boldness of each signal line of the printed wiring SL1 depends upon the width "L2", namely, the scanning range.

Figure 9A:
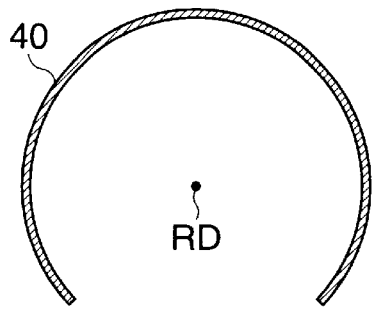
FIGS. 9A to 9C are section views of the flexible circuit board in the point-base portion and the bending portion.
Figure 9B:
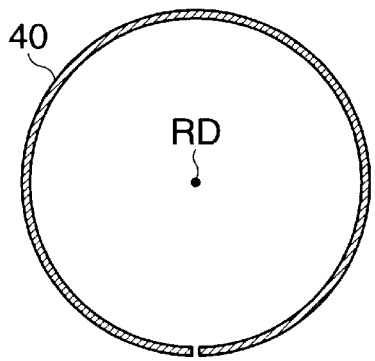
Figure 9C:
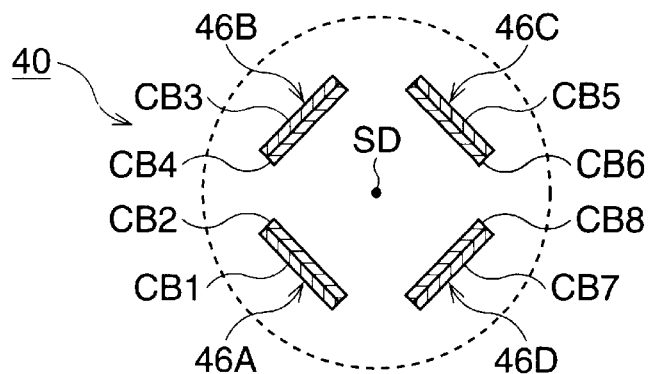

FIGS. 9A to 9C are section views of the flexible circuit board 40 in the point-base portion 13 and the bending portion 12. FIG. 9A is a section view at the line II–II', FIG. 9B is a section view at line III–III', and FIG. 9C is a section view at line IV–IV'. Note that, the lines II–II', III–III', IV–IV' are shown in FIGS. 3 and 7. The section view at the line II–II' is a section view in the point-base portion 13 and near to the ultrasonic probe 14. On the other hand, the section view at line III–III' is a section view in the point-base portion 13 and near to the bending portion 12. A section view at line IV–IV' is a section view in the bending portion 12. Lines B1–B1', C1–C1', D1–D1', shown in FIG. 8, correspond to the lines II–II', III–III', IV–IV', respectively.

As shown in FIG. 9A, the flexible circuit board 40 is formed in an arc, approximately 270 degrees, in accordance with the arc-shaped ultrasonic wave sender-receiver 41, namely, the scanning range. On the other hand, the flexible circuit board 40 is formed in a circle at the line III–III' (See FIG. 9B). Then, as shown in FIG. 7 and FIG. 9C, a circuit board strip and an adjacent circuit board strip among the eight circuit board strips CB1 to CB8, are bundled so that they form four couples or bundles 46A, 46B, 46C, and 46D. The circuit board bundle 46A is composed of the two circuit board strips CB1 and CB2. Similarly, the circuit board bundles 46B, 46C and 46D are composed of the two circuit board strips CB3 and CB4, CB5 and CB6, CB7 and CB8, respectively. At the neighborhood of the flexible tube 11, the four circuit board bundles 46A to 46D are again separated into the eight circuit board strips CB1 to CB8.

Figure 10:
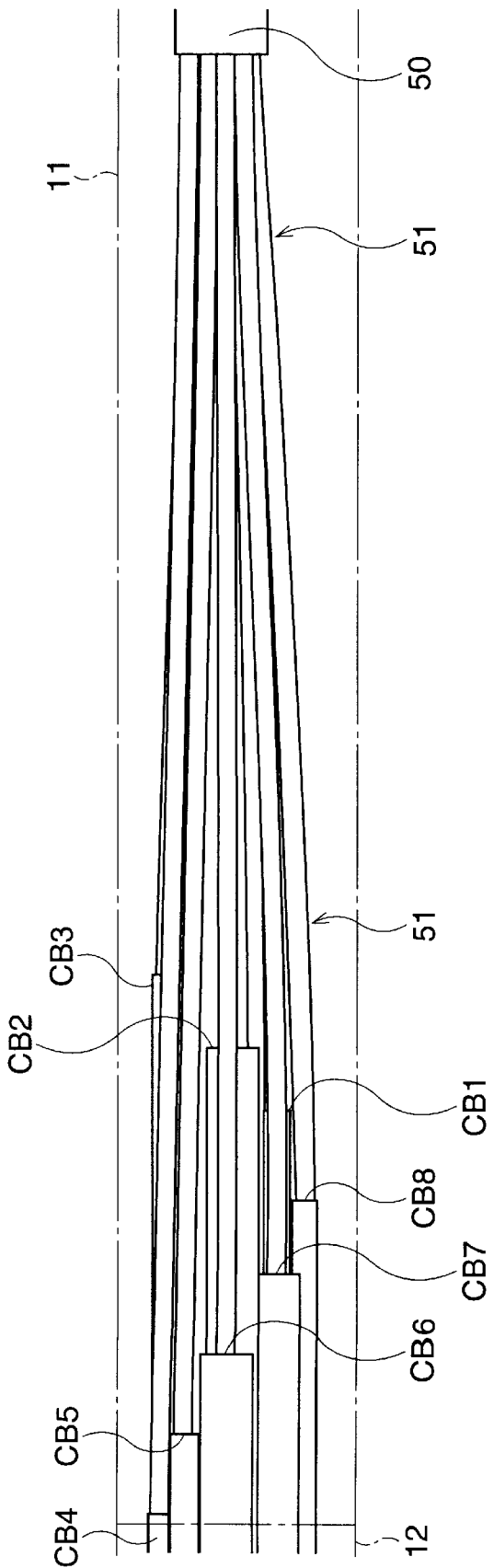
FIG. 10 is a schematic view of the signal lines in the flexible tube.

FIG. 10 is a view showing the signal lines in the flexible tube 11 schematically. The separated eight circuit board strips CB1 to CB8 are connected to eight signal lines 51. The eight signal lines 51 are bundled and formed as an ultrasonic wave single cable 50, which extends between the flexible tube 11 and the second connecter 80B.

Figure 11:
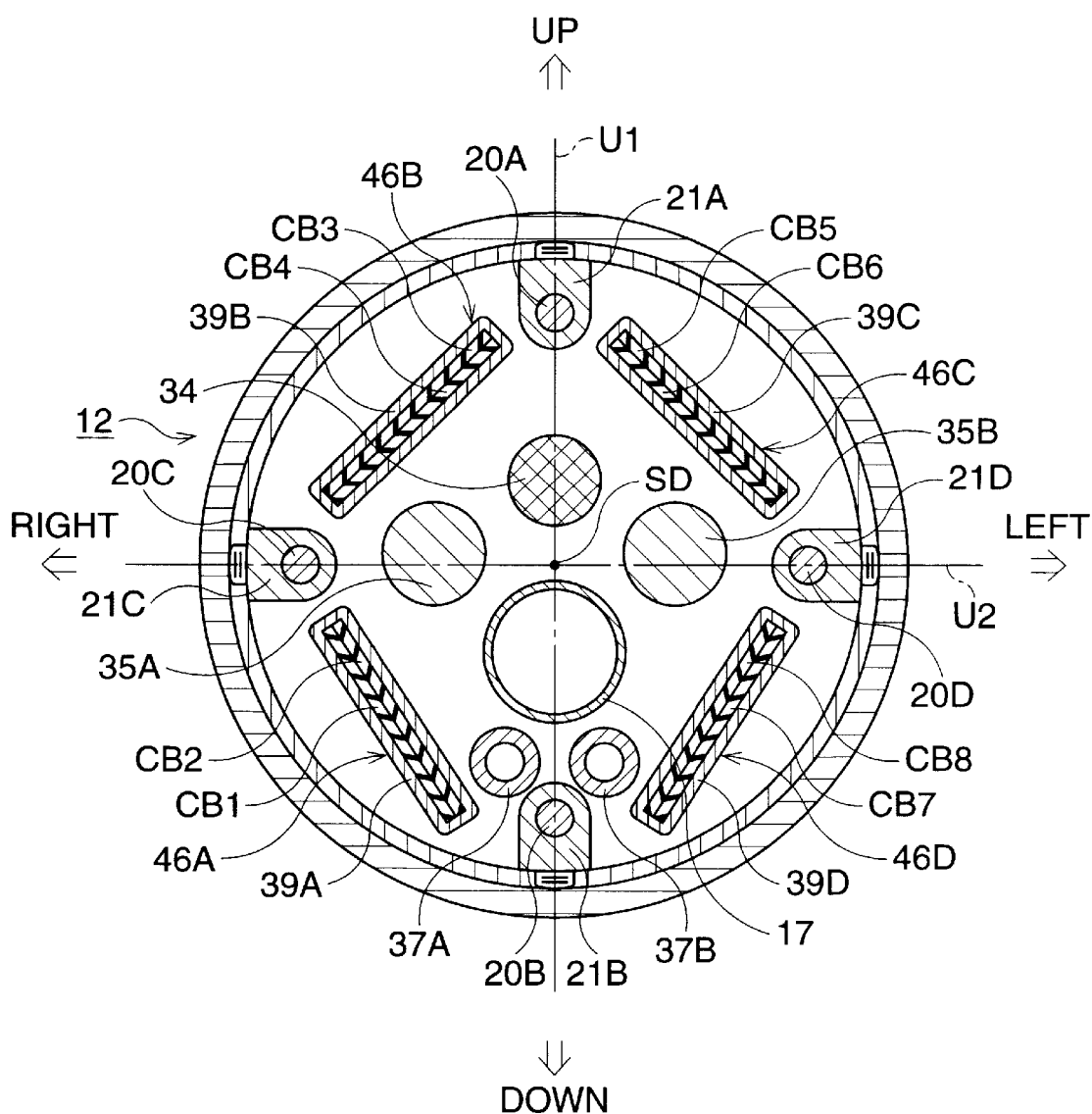
FIG. 11 is a section view of the bending portion, seen from the point side.

FIG. 11 is a section view of the bending portion 12, seen from the point side.

Wire guides 21A, 21B, 21C, 21D are provided between the manipulator portion 15 and the bending portion 12, and are arranged along the circumference of the flexible tube 11 and the bending portion 12, at intervals of 90 degrees.

The wire guides 21A and 21B are positioned along the up-down direction UD, and the wire guides 21C and 21D are positioned along the left-right direction. The wires 20A, 20B are installed in the wire guides 21A and 21B, respectively. Similarly, the wires 20C and 20D are installed in the wire guides 21C and 21D, respectively. The bending portion 12 bends toward the up or down direction by moving the wires 20A and 20B operatively connected to the up-down knob 16A, and bends toward the left or right direction by moving the wires 20C and 20D operatively connected to the left-right knob 16B. As shown in FIG. 11, in the bending portion 12, the forceps tube 17, image signal cable 34, the fiber-optic bundles 35A and 35B, and the delivery tubes 37A and 37B are provided.

The fiber-optic bundles 35A and 35B and the delivery tubes 37A and 37B are arranged so as to have symmetry with respect to a central line U1. Note that, the central line U1, defined in the section of the bending portion and crossing the central axis SD of the bending portion 12, corresponds to the up-down direction UD. The image signal cable 34 and the forceps tube 17 are arranged on the up-down central line U1 so as to have symmetry with respect to the central line U1. Note that, a left-right central line U2, defined in the section passing the central axis SD and perpendicular to the up-down central line U1, corresponds to the left-right direction.

As described above, in the bending portion 12, the flexible circuit board 40 is shaped in the four circuit board bundles 46A, 46B, 46C, and 46D. The circuit board bundle 46A is covered with a flexible heat shrinking tube 39A so that the circuit board bundle 46A and the heat shrinking tube 39A are unified. Similarly, the circuit board bundles 46B, 46C, and 46D are covered with heat shrinking tubes 39B, 39C, and 39D, respectively.

The circuit board bundles 46A, 46B, 46C, and 46D are arranged around the image signal cable 34, the fiber-optic bundles 35A and 35B, the delivery tubes 37A and 37B, and the forceps tubes 17, and are arranged generally along straight lines connecting the four wires 20A, 20B, 20C, and 20D. Therefore, the four circuit board bundles 46A, 46B, 46C, and 46D are at an angle of an generally 45 degrees to the up-down central line U1, and are not arranged on the central line U1. Further, the four circuit board bundles 46A, 46B, 46C, 46D are arranged so as to have symmetry with respect to the up-down central line U1 and the left-right central line U2.

In the bending portion 12, powder lubricants, such as a molybdenum disulfide, are filled. Therefore, the positions of the four circuit board bundles 46A, 46B, 46C, 46D, the image signal cable 34, the fiber-optic bundles 35A and 35B, the delivery tubes 37A and 37B and the forceps tube 17 do not substantially change while moving the bending portion 12.

In this way, in this embodiment, the ultrasonic wave sender-receiver 41 is formed along the circumference of the ultrasonic probe 14, namely, the plurality of ultrasonic wave vibratos are arranged along the circumference. The ultrasonic waves are sent radially around the central axis of the point RD for performing the electronic radial scanning. Then, the flexible circuit board 40 is provided for transmitting the signals associated with the ultrasonic waves and the echoes. In the bending portion 12, the flexible circuit board 40 is constructed of the eight circuit board strips CB1 to CB8, and unified in the four circuit board bundles 46A, 46B, 46C, and 46D.

Further, the four circuit board bundles 46A, 46B, 46C, 46D are arranged so as to have symmetry with respect to the up-down central line U1 in the section of the bending portion 12. Namely, the image signal cable 34, the fiber-optic bundles 35A and 35B, the delivery tubes 37A and 37B and the forceps tube 17, and the four circuit board bundles 46A, 46B, 46C, and 46D are arranged so as to have symmetry with the up-down central axis U1. Thus, the bending-resistance, which occurs when bending the bending portion 12 along the up-down direction, becomes symmetrical with respect to the up-down central line U1. In other words, a flexural rigidity with respect to the up-down central line U1 is symmetrical. Therefore, when the up-down knob 16A is manipulated, the bending portion 12 securely bends along the up-down direction UD without tending to move in another direction.

Figure 12:
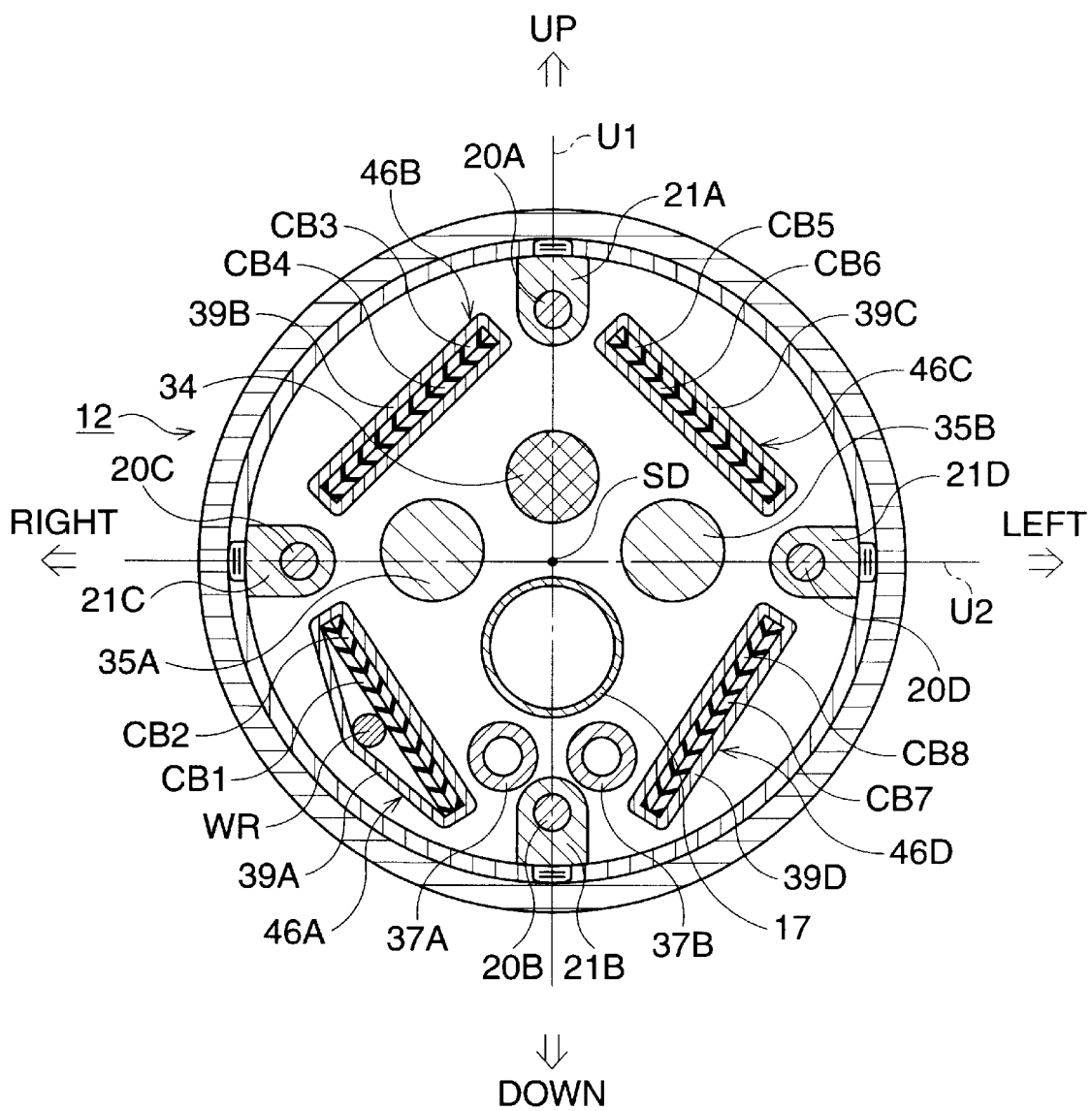
FIG. 12 is a view showing a section of the bending portion, in which the resistance member is provided.

Note that, to perfectly produce bending-resistance symmetrically, a resistance member, such as a coil, wire, may be attached on a flexible circuit board strip. FIG. 12 is a view showing the section of the bending portion 12, in which the resistance member is provided. To produce the bending resistance symmetrically with respect to the up-down central line U1, a wire WR, extending along the central axis SD of the bending portion 12, is provided in the heat shrinking tube 39A and is attached on the flexible circuit board strip CB2.

Figure 13:
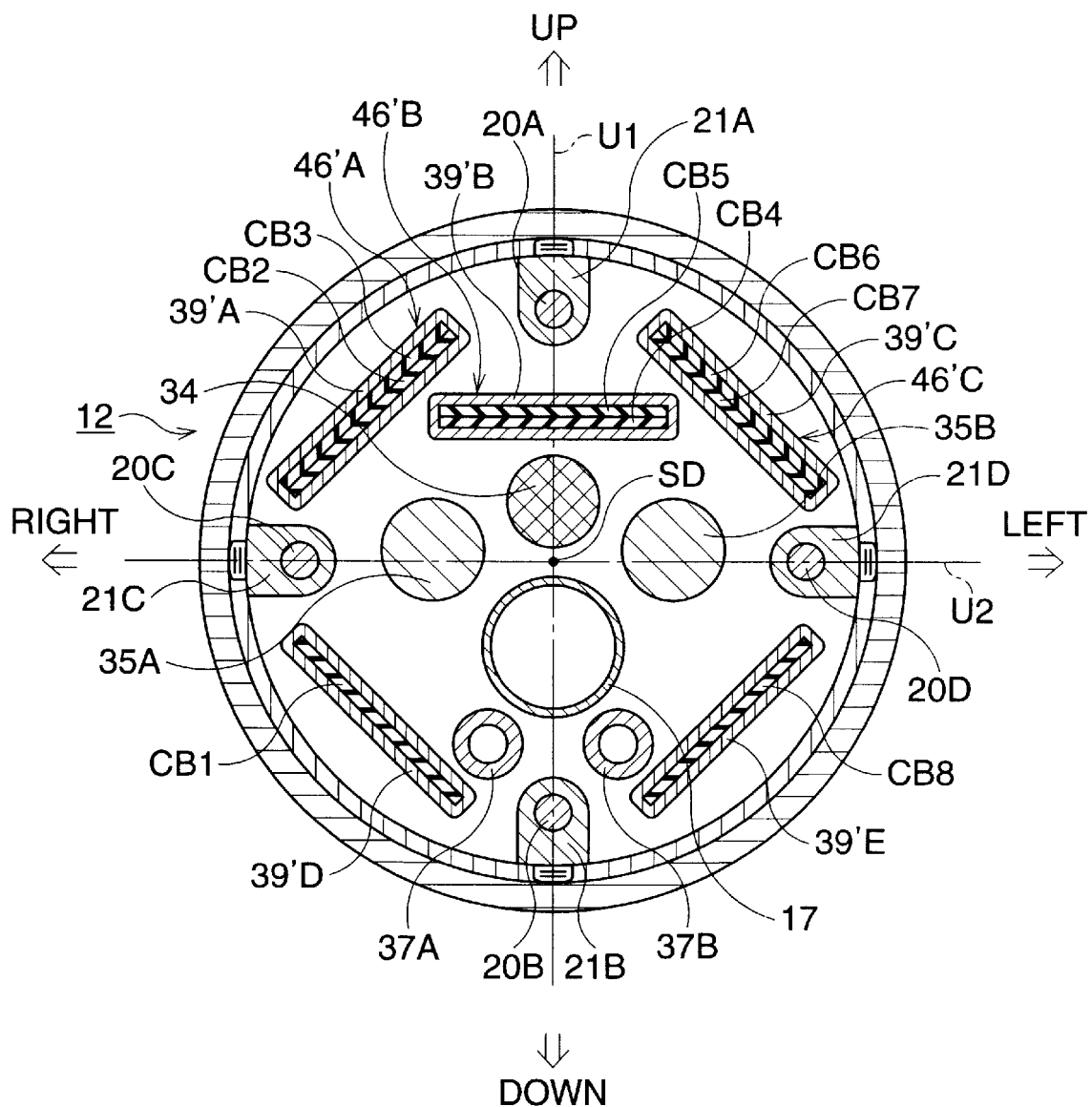
FIG. 13 is a section view of a bending portion of a second embodiment.

With reference to FIG. 13, an ultrasonic endoscope of a second embodiment is explained. The second embodiment is different from the first embodiment with respect to an arrangement of the flexible circuit board strips.

FIG. 13 is a section view of a bending portion of the second embodiment.

In the second embodiment, the eight flexible circuit board strips CB1 to CB8 are separated into three circuit board bundles, each of which has two circuit board strips, and two independent circuit board strips. The circuit board bundle 46'A is composed of the circuit board strips CB2 and CB3, the circuit board bundle 46'B is composed of the circuit board strips CB4 and CB5, and the couples of circuit board bundle 40'C are composed of the circuit board strips CB6 and CB7. The two circuit board strips CB1 and CB8 independently extend along the central axis SD. The three circuit board bundles 46'A, 46'B, and 46'C are covered with heat shrinking tubes 39'A, 39'B, 39'C respectively. The two circuit board strips CB1 and CB8 are covered with heat shrinking tubes 39'D and 39'E, respectively. The three circuit board bundles 46'A, 46'B, and 46'C, and the two circuit board strips CB1 and CB8, are arranged such that the bending-resistance occurs symmetrically with respect to the up-down central line U1.

In this way, in the bending portion 12, the flexible circuit board strips CB1 to CB8 may be arbitrarily bundled or independent without bundling.

In the first and second embodiments, the eight circuit board strips CB1 to CB8 are formed by partially cutting the single rectangular flexible circuit board 40'. However, the flexible circuit board 40' may be partially cut such that the number of circuit board strips is a number other than eight (for example, twelve). Further, in place of utilizing a partially-cut flexible circuit board 40', the flexible circuit board 40 may be composed of a plurality of flexible circuit board strips. In this case, each of the flexible circuit board strips is connected to the ultrasonic wave sender-receiver 41. The thickness and width of each circuit board strips may be defined in accordance with the radius of the bending portion.

In the embodiments, the image signal cable 34, the fiber-optic bundles 35A and 35B, the delivery tubes 37A and 37B, and the forceps tube 17 are arranged so as to have symmetry with the up-down central line U1. When these members are not arranged symmetrically with respect to the up-down central axis U1 respectively, the plurality of circuit board strips may be arranged such that the bending-resistance occurs symmetrically with respect to the up-down central line U1 in the bending portion 12. At this time, the plurality of circuit board strips is arranged on the basis of the unsymmetrical arrangement of these members. Further, the plurality of flexible circuit strips may be arranged such that the bending-resistance occurs symmetrically with respect to the left-right central line U2. For example, when the image signal cable 34, the fiber-optic bundles 35A and 35B, the delivery tubes 37A and 37B, and the forceps tubes 17 are arranged so as to have symmetry with the left-right central line U2, the four circuit board bundles 46A, 46B, 46C, and 46D may be arranged symmetrically with respect to the up-down and left-right central lines U1 and U2.

Finally, it will be understood by those skilled in the art that the foregoing description is of preferred embodiments of the device, and that various changes and modifications may be made to the present invention without departing from the spirit and scope thereof.

The present disclosure relates to subject matters contained in Japanese Patent Application No.2000-353739 (filed on Nov. 21, 2000) which is expressly incorporated herein, by reference, in its entirety.

What is claimed is:

1. An ultrasonic endoscope comprising:

a bending portion in a tube and connected to a flexible tube insertable into a body, said bending portion being bent along two predetermined bending-directions perpendicular to each other, by remote control;

an ultrasonic probe operatively connected to said bending portion and comprising a plurality of ultrasonic wave vibrators arranged circumferentially, said plurality of ultrasonic wave vibrators sending ultrasonic waves radially and receiving echoes of the ultrasonic waves; and a flexible circuit board that transmits signals associated with the ultrasonic waves and the echoes, said flexible circuit board comprising a plurality of flexible circuit board strips in said bending portion so as to allow a bending motion, said plurality of flexible circuit board strips extending along a central axis of said bending portion, wherein said plurality of flexible circuit board strips are arranged such that a bending-resistance to the bending motion occurs symmetrically with respect to a primary central line, which is defined on a bending section of said bending portion, which crosses said central axis and corresponds to one of said two bending-directions.

2. The ultrasonic endoscope of claim 1, wherein said plurality of flexible circuit board strips are arranged so as to have line symmetry with respect to said primary central line in said bending section.

3. The ultrasonic endoscope of claim 2, wherein width and thickness of each of said plurality of circuit board strips in said bending section are substantially the same.

4. The ultrasonic endoscope of claim 2, wherein a plurality of bundles, each of which is composed of at least two flexible circuit board strips, is formed for said plurality of flexible circuit board strips.

5. The ultrasonic endoscope of claim 2, wherein said plurality of circuit board strips are arranged along the central axis such that a section form of each of said plurality of circuit board strips becomes substantially a straight-shape.

6. The ultrasonic endoscope of claim 2, wherein said plurality of circuit board strips are arranged such that said plurality of circuit board strips are not on said primary central line in said bending section.

7. The ultrasonic endoscope of claim 2, further comprising:

a fiber-optic bundle for transmitting light;

a delivery tube for delivering liquid;

a forceps tube for installing a forceps; and an image signal cable for transmitting image signals, wherein each of said fiber-optic bundle, said delivery tube, said forceps tube, and said image signal cable is arranged so as to have line symmetry with respect to said primary central line in said bending section.

8. The ultrasonic endoscope of claim 2, wherein said flexible circuit board comprises a single rectangular flexible circuit board having an arcuate shape, said plurality of flexible circuit board strips being defined by slits in said flexible circuit board.

9. The ultrasonic endoscope of claim 8, wherein said plurality of flexible circuit board strips are composed of eight circuit board strips, each width of which is the same.

10. The ultrasonic endoscope of claim 9, wherein said eight circuit board strips are bundled so that two adjacent circuit board strips form one bundle.

11. The ultrasonic endoscope of claim 1, wherein each of the plurality of flexible circuit board strips is provided along said central axis and is arranged so as to have a symmetry with respect to said primary central line in said bending section.

* * * * *